United States Patent
Barney et al.

(10) Patent No.: US 8,651,103 B2
(45) Date of Patent: Feb. 18, 2014

(54) DRY POWDER INHALATION APPARATUS

(75) Inventors: Brian Barney, Essex (GB); David O'Leary, Essex (GB); Rachel Striebig, London (GB)

(73) Assignee: Norton Healthcare Ltd., London (GB)

( * ) Notice: Subject to any disclaimer, the term of this patent is extended or adjusted under 35 U.S.C. 154(b) by 1271 days.

(21) Appl. No.: 10/574,386

(22) PCT Filed: Oct. 2, 2004
(Under 37 CFR 1.47)

(86) PCT No.: PCT/US2004/032160
§ 371 (c)(1),
(2), (4) Date: Apr. 21, 2008

(87) PCT Pub. No.: WO2005/034833
PCT Pub. Date: Apr. 21, 2005

(65) Prior Publication Data
US 2008/0314383 A1    Dec. 25, 2008

(30) Foreign Application Priority Data

Oct. 2, 2003 (GB) .................................. 0323085.1

(51) Int. Cl.
*A61M 16/00* (2006.01)
*A61M 15/00* (2006.01)

(52) U.S. Cl.
USPC .................................. 128/203.15; 128/203.19

(58) Field of Classification Search
CPC ............ A61M 15/00; A61M 15/0065; A61M 15/0091; A61M 16/208
USPC ............. 128/203.19, 203.12, 203.15, 203.21, 128/203.23, 205.24
See application file for complete search history.

(56) References Cited

U.S. PATENT DOCUMENTS

| 5,033,463 | A | * | 7/1991 | Cocozza | 128/203.21 |
| 5,113,855 | A | * | 5/1992 | Newhouse | 128/203.12 |
| 5,239,992 | A | * | 8/1993 | Bougamont et al. | 128/203.15 |
| 5,429,122 | A | * | 7/1995 | Zanen et al. | 128/203.15 |
| 6,332,461 | B1 | | 12/2001 | Hyppola | |
| 6,672,304 | B1 | * | 1/2004 | Casper et al. | 128/200.23 |
| 2002/0073996 | A1 | | 6/2002 | OLeary | |
| 2002/0078949 | A1 | * | 6/2002 | O'Leary | 128/200.22 |
| 2002/0078950 | A1 | | 6/2002 | OLeary | |

FOREIGN PATENT DOCUMENTS

| WO | 9405359 | 3/1994 |
| WO | 9405360 | 3/1994 |

OTHER PUBLICATIONS

Examination report dated Jun. 25, 2010, Application No. 04793913.7.

* cited by examiner

*Primary Examiner* — Melanie Hand
*Assistant Examiner* — Peter S Vasat
(74) *Attorney, Agent, or Firm* — RatnerPrestia

(57) ABSTRACT

The invention relates to dry powder inhalation apparatus usually operable by breath of a user which provides for controlled and smooth transfer of medicament during multiple actuations by a user. A mechanism of the apparatus for achieving this controlled and smooth transfer includes a device (4) normally held adjacent a reservoir for receiving medicament in a cup or receptacle (15) and which is generally movable transversely of a longitudinal axis of the apparatus to delivery channels of the apparatus. This bodily shifting of the device (4) is achieved by a yoke acting on an abutment (16) thereof. Spillage of medicament in the apparatus is avoided.

37 Claims, 12 Drawing Sheets

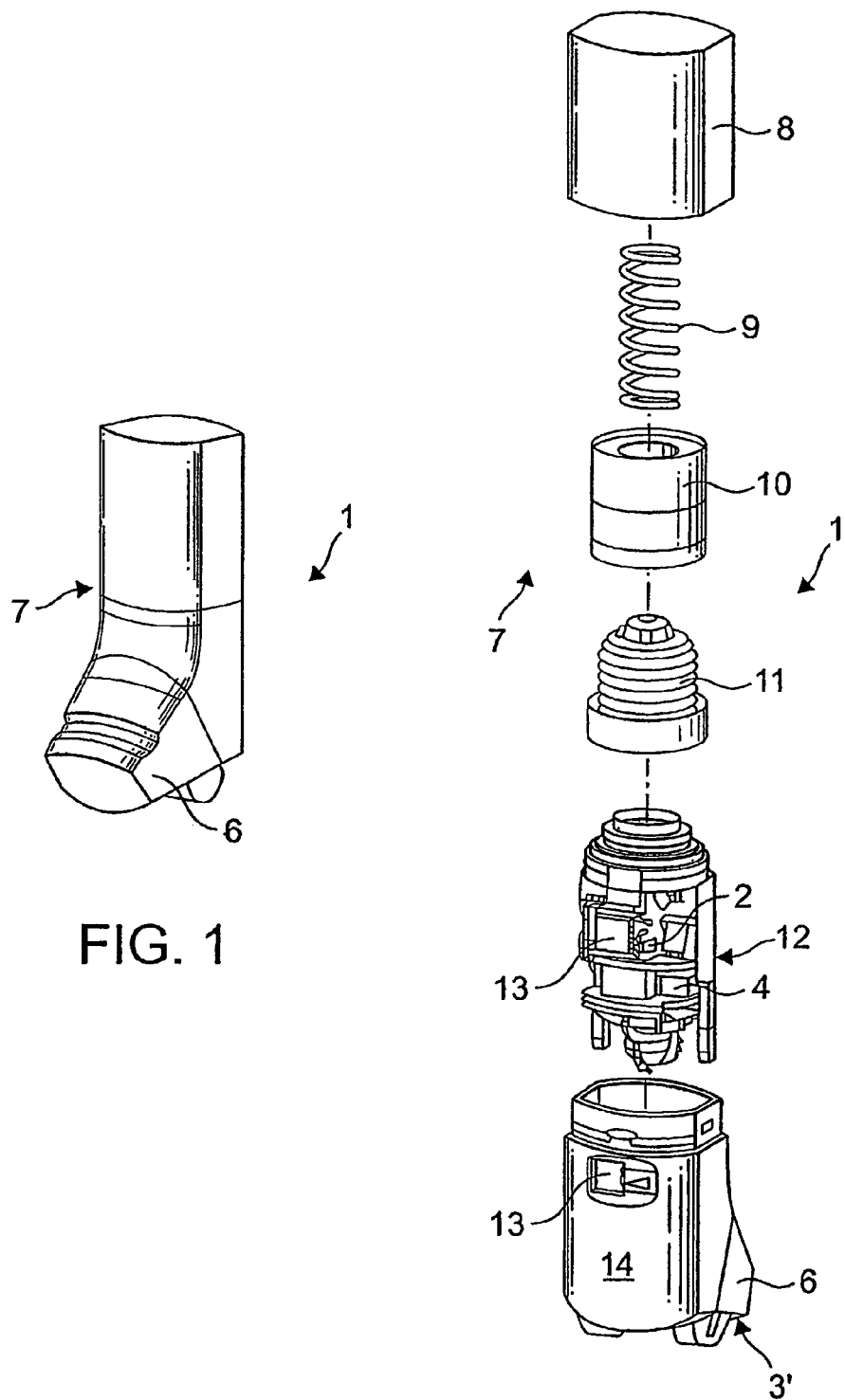

DRY POWDER INHALATION APPARATUS

BACKGROUND OF THE INVENTION

The invention relates to dry powder inhalation apparatus. This apparatus administers a dry powder medicament in a desired predetermined dose to a user of the apparatus who actuates the apparatus manually and then breathe in the predetermined dose, or, on taking a breath, would automatically actuate the device for breathing in the predetermined dose of medicament. Breath actuation is typically used to dispense the desired dose of medicament into the lungs of the patient. The medicament is carried in air during inhalation so that fine particles are carried into the lungs and heavier particles are retained in the buccal cavity.

Typically such an apparatus includes a reservoir for containing the medicament in dry powdered form. The reservoir contains medicament for a particular number of doses. The doses are metered from the reservoir one dose at a time on actuation by a user. The apparatus also includes an air inlet or inlets for taking up or entraining the medicament for passage along airways through a mouthpiece of the apparatus and into the lungs of the user when the user takes a breath.

The amounts of medicament in a particular dose are small and received from the reservoir in a device having a receptacle or cup for receiving a metered dose of medicament. The device then shifted bodily in order to transfer the metered dose to the air channels. The body of the device seals off a discharge outlet from the reservoir during this transfer motion.

In known apparatus, a mechanism transfers a slide carrier assembly carrying a metered dose by releasing the slide carrier off the end of a lower ledge of a yoke. A yoke lower moves as a trigger is rotated by a mouthpiece cover opening. The trigger has two drop zones. The first of these is used to generate sudden movement of the yoke lower to compress a bellows for metering. The second drop zone is also sudden, and it is during this zone that the yoke lower releases the slide carrier. The transfer spring forces the slide carrier across a channel between a hopper upper and a hopper lower components. When the slide carrier hits the side wall of the hopper upper the slide carrier stops abruptly.

However, even though a relatively small amount of powder is being dispensed, the powder making up each dose can be compacted which can cause more than the prescribed dosage to be received in the cup.

Moreover, even if there is no compaction, the medicament can be spilled from the cup on transfer. Consequently, although there is a collection well for receiving spilled medicament, the required desired dosage may not be administered when the user takes a breath.

Both disadvantages of compaction and spillage result from the way in which the device is transferred from the discharge outlet of the reservoir to the position for passage of the medicament into the air channels.

Accordingly, the present invention mitigates these disadvantages.

SUMMARY OF THE INVENTION

According to the present invention, there is provided dry powder inhalation apparatus, comprising a reservoir for medicament, a mouthpiece for insertion in the mouth of a user for inhalation of a predetermined dose of medicament, a delivery channel between a discharge outlet of the reservoir and the mouthpiece for delivering said predetermined dose of medicament, a device normally held adjacent the reservoir for receiving said predetermined dose of medicament from said discharge outlet and transferring it to the delivery channel, and a mechanism adapted to release the device and permit controlled movement thereof to the delivery channel for said delivery.

It will be understood that in using the invention it is possible to provide for controlled, smooth transfer of a required dose of medicament in a two-stage operation. Movement of the device is interrupted after charging with medicament for subsequent controlled movement to the position for passage of the medicament into air channel(s) forming the discharge channels.

The device may comprise a cup for receiving said dose and a longitudinally slidable body mounting said cup, the mechanism comprising abutment means which is movable to release the device for movement to the delivery channel.

The abutment means may preferably be bodily movable by an actuation means. This provides for positive operation and actuation.

The abutment means may also comprise a resilient member which is flexible out of the path of the device. This again provides a positive operation and actuation particularly when the resilient member may comprise a one piece member of substantially J- or U-configuration, one limb of which is movable for releasing the device.

The movable limb may have a finger-operable tab projecting from a housing apparatus, and the tab may have indicia indicating the direction of flexing of the limb for release of the device.

The actuation means may comprise a resiliently mountable slidable member which has a tab projecting through a bore of a body of the apparatus for releasing the device. This also provides for positive operation and actuation, the slidable member preferably having indicia which can be read through the bore for indicating the position of the device. The indicia may suitably comprise a colour code indicia.

The actuation means may further comprise a resiliently and pivotably mounted detent means which is shiftable bodily about its pivot axis to release the device.

Suitably, the detent means may have a finger grippable projection which projects therefrom and through a slot in the body of the apparatus for bodily shifting of the detent when the projection is moved along the slot.

The actuating means may further comprise a resiliently mounted plunger means which has one end projecting through a bore in a body of the device and an opposite end adapted to engage the device for shifting same bodily to said delivery channel.

The plunger means may suitably have a substantially cylindrical body member connecting the one end and the opposite end, and the opposite end may be enlarged relative to the body member.

There may be a relatively soft cushion member of the opposite end for contacting the device. This provides for a cushioned, controlled motion of the device.

The actuation means may comprise an electrical electronic or electro-mechanical means.

The actuation means may comprise a solenoid means actuated by a switch device for actuation of the device. Suitably, the switch device may be operable manually by a user, or alternatively the switch device may be operable by inhalation of a breath by a user. In either mode, a positive operation of the device can be achieved.

There may be a power source for the electrical, electronic or electro-mechanical means.

There may be a cover for an end of the discharge channel at the mouthpiece, and the cover may be movable between a position covering the discharge channel and a position for discharging said dose, whereby to allow actuation of the mechanism.

The cover may suitably comprise a relatively rigid disc carried by opposed arms which at an end thereof opposite the disc mount a cam which has a profile for allowing movement of a cam follower in a direction away from the device whereby to allow operation of the actuation means for bodily movement of the abutment means.

The disc in its first mentioned position may be housed within a guard of the apparatus, which guard is pivotably mounted for access to the disc.

There may be a yoke member which is shiftable bodily towards and away from the mouthpiece and mounting limbs, one of which has a cam follower for following a cam which is rotatable for actuation of the yoke member which carries the actuation means in the form of a ramp up which a part at least of the device can travel for controlled movement thereof towards the delivery channel. This again provides a positive operation, particularly when the actuation means comprises a return element for returning the device to the charging position.

Such a return element may suitably comprise an inclined ledge down which the part travels to said discharge outlet.

The apparatus may be a breath actuable apparatus.

The mechanism may be between opposed spaced walls of the reservoir and may have a member which may be retractable on a user taking a breath on the mouthpiece.

The mechanism may comprise cooperating rotatable means one of which has a detent for engaging the device and the other of which is operable to maintain the detent in engagement with the device and to allow rotation of the one means to release the detent and device.

The mechanism may further comprise a stop member, retractable as a user taking a breath on the mouthpiece, and adapted to release the other rotatable means and the detent.

The rotatable means may comprise cam or gear means.

The stop member may suitably comprise an elongate mounted member which is biased to engage the other rotatable means and a flap valve which is operable to allow air into a space between said opposed walls to equalise air pressure inside and outside the space and bias the elongate members to operate the cam or gear means.

The device may be mounted under pressure resilient means, suitably spring means.

There may also be damper means for damping movement of the device.

Embodiments of the apparatus according to the invention are hereinafter described, by way of example, with reference to the accompanying drawings.

BRIEF DESCRIPTION OF THE DRAWINGS

FIG. 1 shows a perspective view of a typical dry powder inhalation apparatus;

FIG. 2 shows an exploded perspective view of a typical dry powder inhalation apparatus like that of FIG. 1;

DETAILED DESCRIPTION OF THE INVENTION

Figure 3:
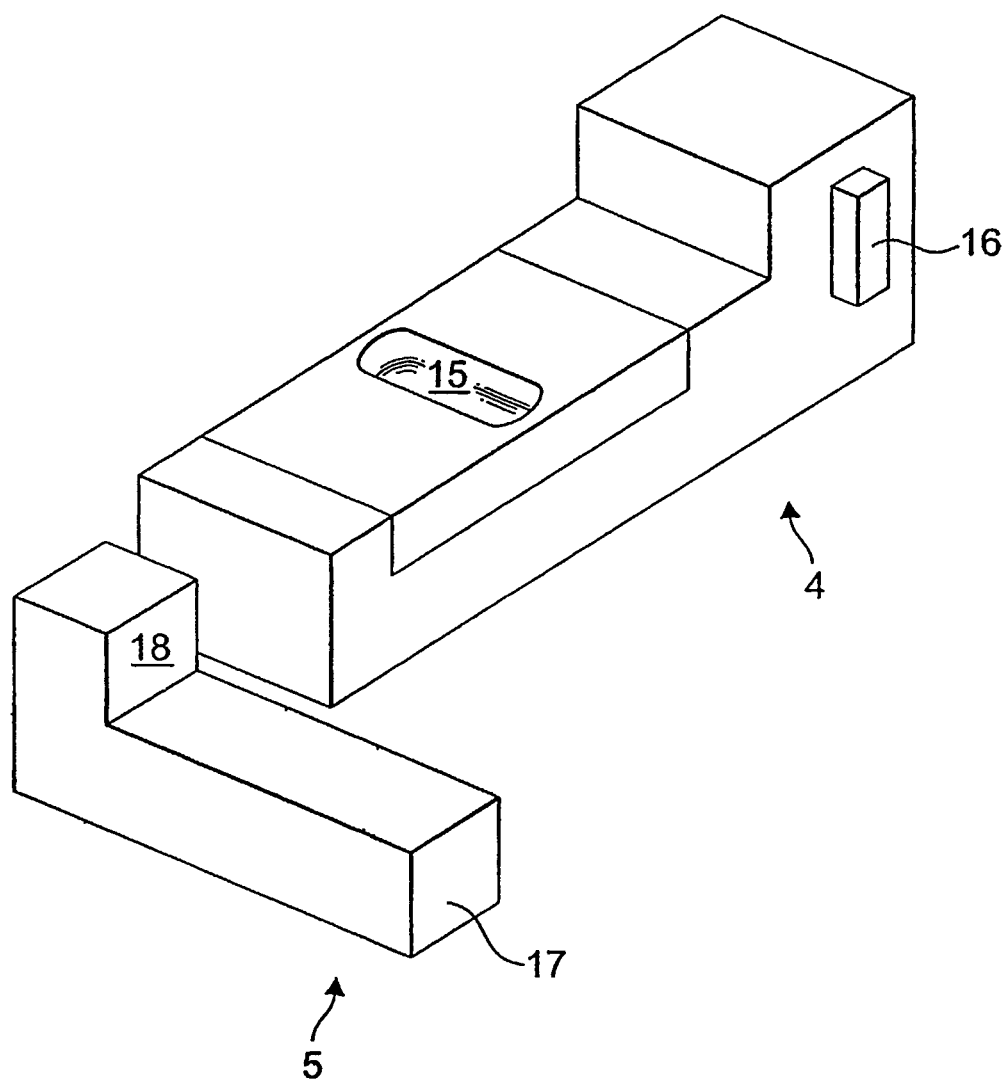
FIG. 3 shows to a much enlarged scale a perspective view of an embodiment of device for dispensing a desired dose of medicament according to the invention.

Referring to the drawings (see for example FIGS. 1, 2, 3, 9), and in which like parts are referred to by like numerals where feasible, there is shown dry powder inhalation apparatus 1, comprising a reservoir 2 for medicament, a mouthpiece 3' for insertion in the mouth of a user for inhalation of a predetermined dose of a medicament, a delivery channel 3 between a discharge outlet 4' of the reservoir 2 and the mouthpiece for delivering said predetermined dose of medicament, a device 4 normally held adjacent the reservoir for receiving a predetermined dose of medicament from said discharge outlet and transferring it to the delivery channel, and a mechanism 5 adapted to release the device 4 and permit controlled movement thereof to the delivery channel for said delivery.

FIG. 1 shows the general outline of the inhalation apparatus 1 from in front there being a pivotable cover 6 at the bottom (and as used) of a body 7 of the device.

As shown in FIG. 2, the housing or body 7 of the apparatus 1 includes a cap 8, an internal spring 9, a yoke 10, a bellows 11, an actuating mechanism including a further yoke 12, a counter 13, viewable in the base 14 of the body 7 mounting the mouthpiece cover 6.

The mechanism 5 (FIG. 3. and FIG. 12 for example) includes the device 4 which is generally movable transversely of a longitudinal axis of the apparatus 1 for receiving in a cup or receptacle 15 a metered dose of powdered medicament which is then transferred by the shifting of the device 4 to the discharge channels or airways 3 which when a patient breathes in on sucking on the mouthpiece 3', removes the powdered metered dose from the cup or receptacle 15 so that it is entrained in the air and passes through the mouthpiece 3' into the lungs and mouth of the user. Charging of the cup or receptacle 15 with medicament is effected from a discharge outlet 4' (FIG. 12) of the reservoir 2 by the bellows 11 on movement of the yoke 10 in a position towards the mouthpiece 3', there being a part in the form of a shoulder, boss or abutment 16 of the device 4, for shifting the device longitudinally bodily from the discharge outlet 4' to the air delivery channel 3.

In order to provide a smooth operation, there is positioned at the fore end of the device 4 an abutment 5 which has physically to be moved bodily out of the way of the device and, as shown in FIG. 3, this abutment is of L-shape which on movement by finger pressure on an end 17 shifts the abutment 5 so that an upstanding integral part 18 thereof is clear of the adjacent end of the device 4 so that the device 4 can then be moved smoothly to the discharge position under pressure of a spring (which is not shown).

Figure 4:
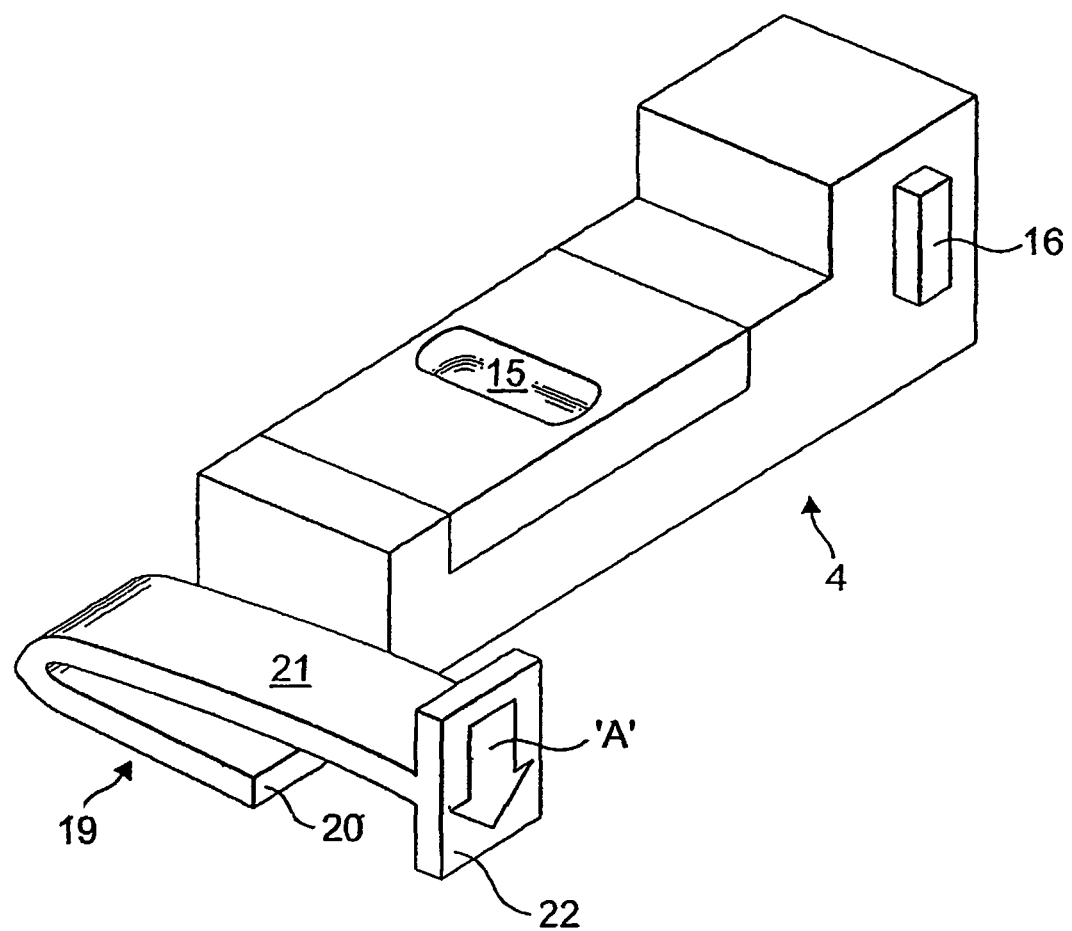
FIG. 4 shows to a much enlarged scale a perspective view of a second embodiment of device for dispensing a desired dose of medicament according to the invention.

FIG. 4 shows a further embodiment in which the abutment comprises a resilient member 19 in the form of in the embodiment shown a J-shaped plastic spring-like member, the lower or shorter limb 20 of which is secured in the body 7 of the apparatus 1 and the upper limb 21 of which is able to be flexed out of the path of the device 4 on movement of a tab 22 downwardly as shown by the indida 'A' in the form of an arrow on the outside surface thereof.

When the underside of the longer limb 21 meets the upper surface of the lower limb 20 and therefore cannot be lowered further, the user knows that there is a positive "stop", and the desired medicament is available for inhalation.

Figure 5A:
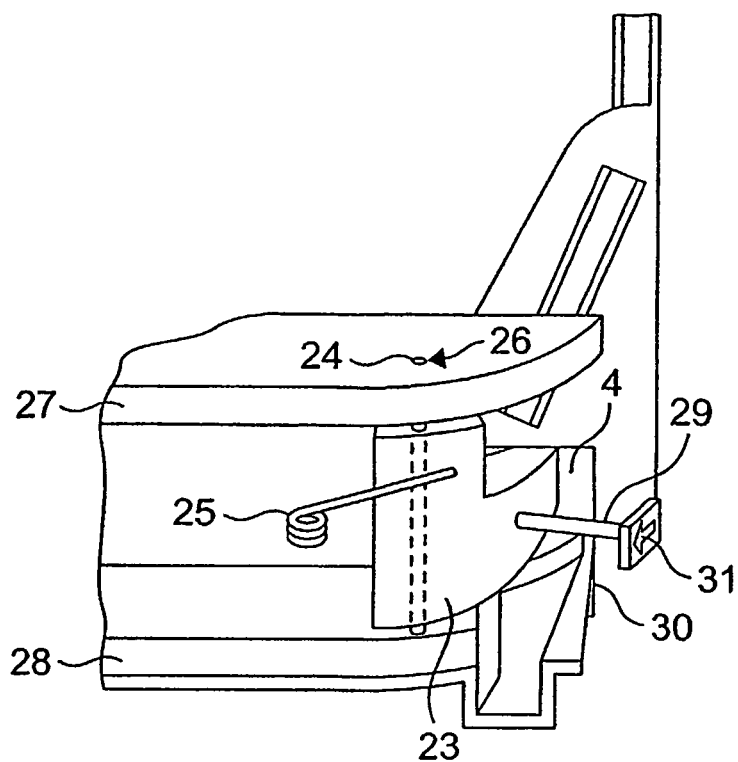
FIGS. 5A and 5B shows respectively two operative positions of a third embodiment of apparatus according to the invention.
Figure 5B:
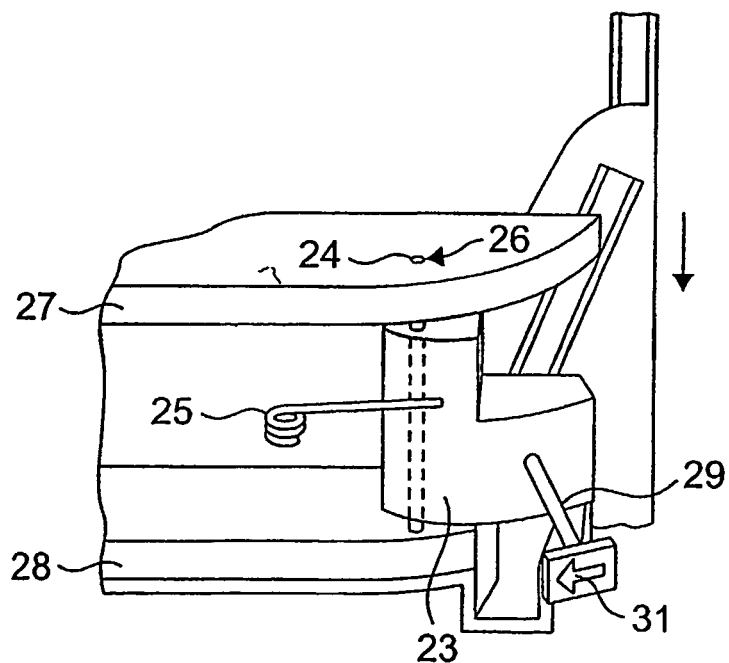

Turning now to FIGS. 5A and 5B, the mechanism 5 includes a pivotable stop 23. The stop 23 is of generally L-shape and is mounted for pivotable movement on an axis 24 under spring pressure 25 which tends to bias it towards a position obstructing movement of the device 4.

The pivot 24 is mounted in holes 26 in facing members of upper and lower flanges 27, 28 of the reservoir or hopper 2.

There is a projection 29 from one limb of the abutment member 23, the projection 29 being accessible manually through an orifice 30 in a wall of the body 7 by a user who on turning the projection 29 in the direction shown by the arrow 31, releases the device 4 for smooth but positive motion to the discharge position, the projection 29 when it meets a blind wall of the orifice 30 effectively informing the user that the desired dosage of medicament is again available for inhalation.

Figure 6:
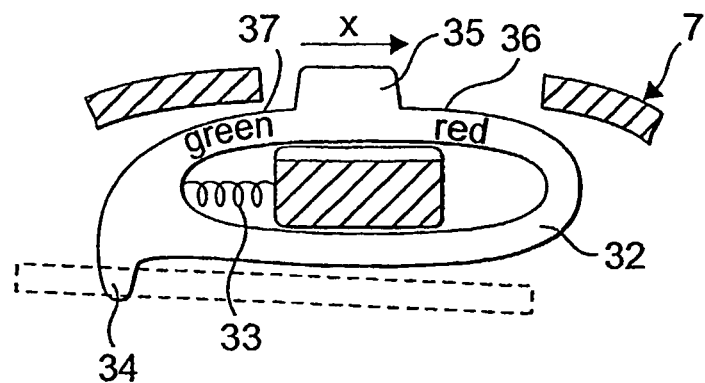
FIG. 6 shows a plan view of a fourth embodiment of apparatus according to the invention.

FIG. 6 shows a yet further embodiment in which there is a slidable ring-shaped member 32 which is mounted under pressure of a spring 33 to be biased to a position in which a projection 34 of the ring 32 interferes with the motion of the device 4. The ring member 32 also includes a button 35 which projects through an opening or orifice 36 in a wall 7 of a body of the apparatus 1.

The ring 32 includes indida 37 either in lettering or in colour, for example in red and green showing when the device 4 is not ready for dispensation (red) or is ready for dispensation and thus inhalation (green).

The user can read this indicia when the button 35 is pushed under finger or thumb pressure from left to right as shown by the arrow 'X' in FIG. 6, thereby releasing the device 4 and thus making the medicament ready for inhalation.

Figure 7:
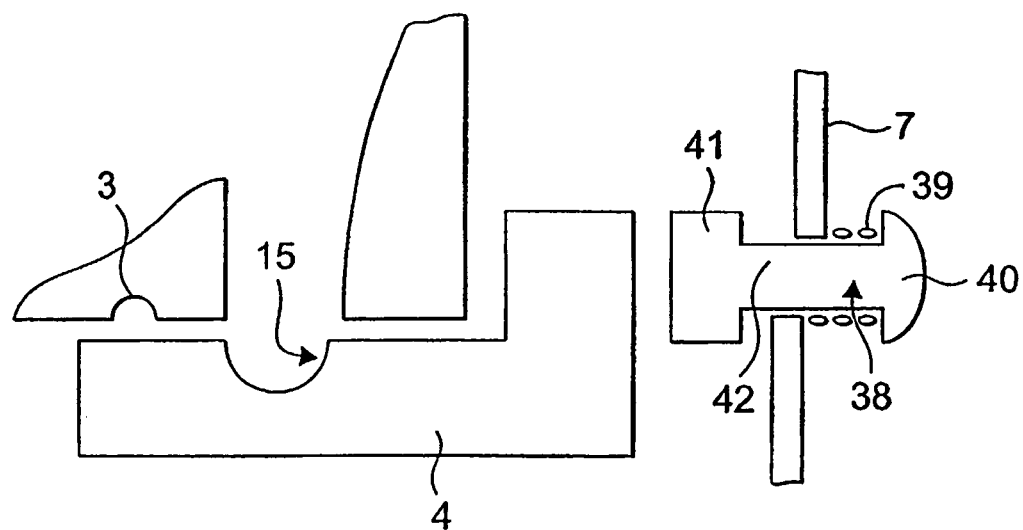
FIG. 7 shows schematically a fifth embodiment of apparatus according to the invention.

Turning now to FIG. 7, an embodiment is shown in which a button or plunger 38 mounted in a wall 7 of the apparatus 1 under spring 39 pressure is biased away from contact with an abutment of the device 4, but on actuation of a head 40 of the plunger inwardly the opposite end 41 thereof which is enlarged relative to a cylindrical body 42 of the plunger contacts the device 4 and shifts it bodily and smoothly to the left as viewed ready for discharge to the air channels, on inhalation.

Release of the button 38 retracts the plunger so that the device 4 itself can return for further charging, the device as in all embodiments, being mounted under spring pressure which biases it towards the charging position. The enlarged opposite end 41 of the plunger 38 may include a cushion (not shown) for providing a cushioned contact of the plunger with the device 4.

Figure 8:
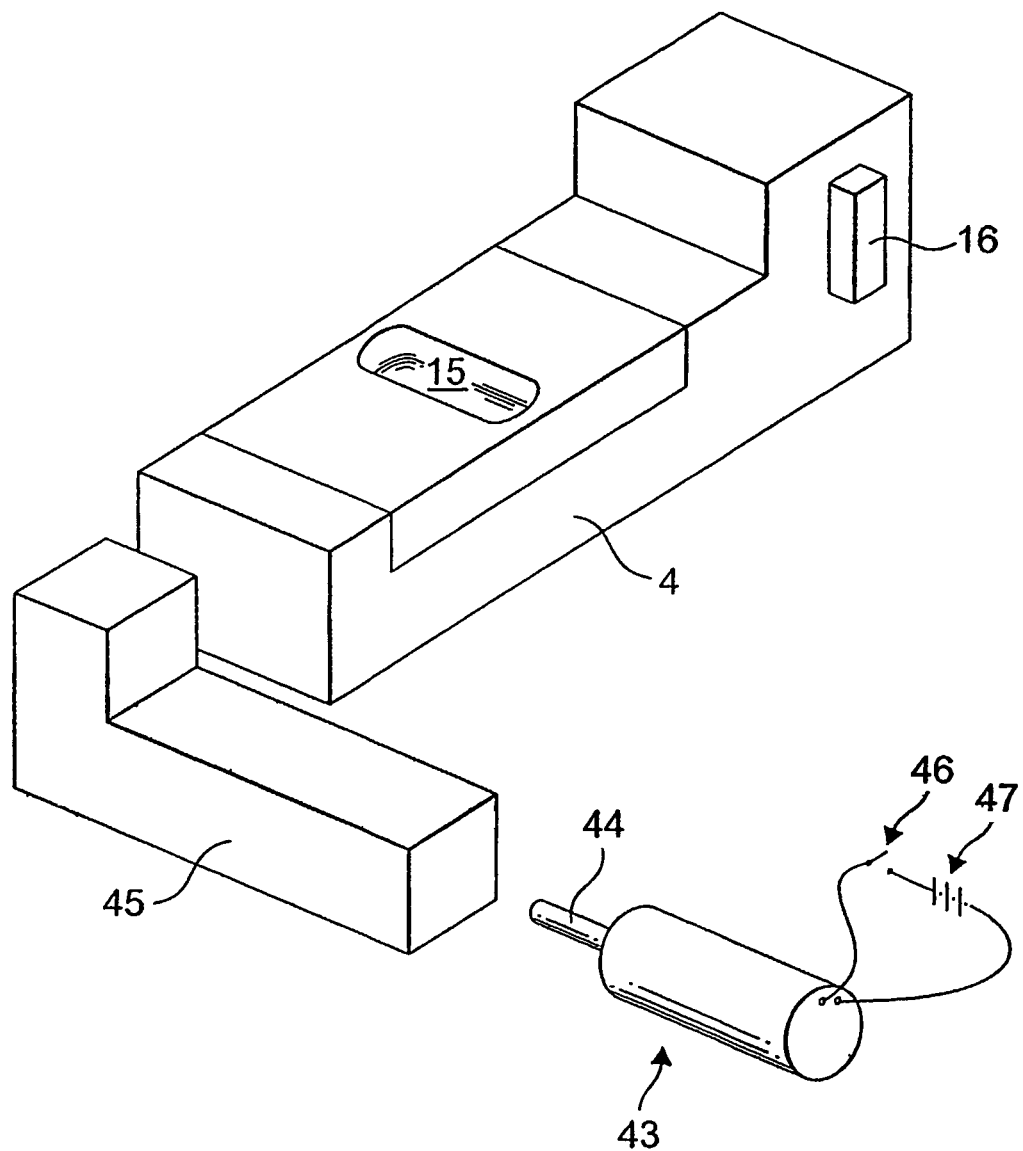
FIG. 8 shows schematically a perspective view of a further embodiment of apparatus according to the invention.

FIG. 8 shows a yet further embodiment in which there is an actuator 43 such as an electrical, electronic or electro-mechanical actuator having an extensible actuating member such as a piston rod 44 which on operation of the actuator 43 extends to push the abutment 45 of the mechanism out of the path of the device 4, for discharge as before. The actuator 43 in this embodiment includes a switch 46, and a power source 47 such as a battery. The switch 46 may be operated manually, or automatically when a user takes a breath.

Figure 9:
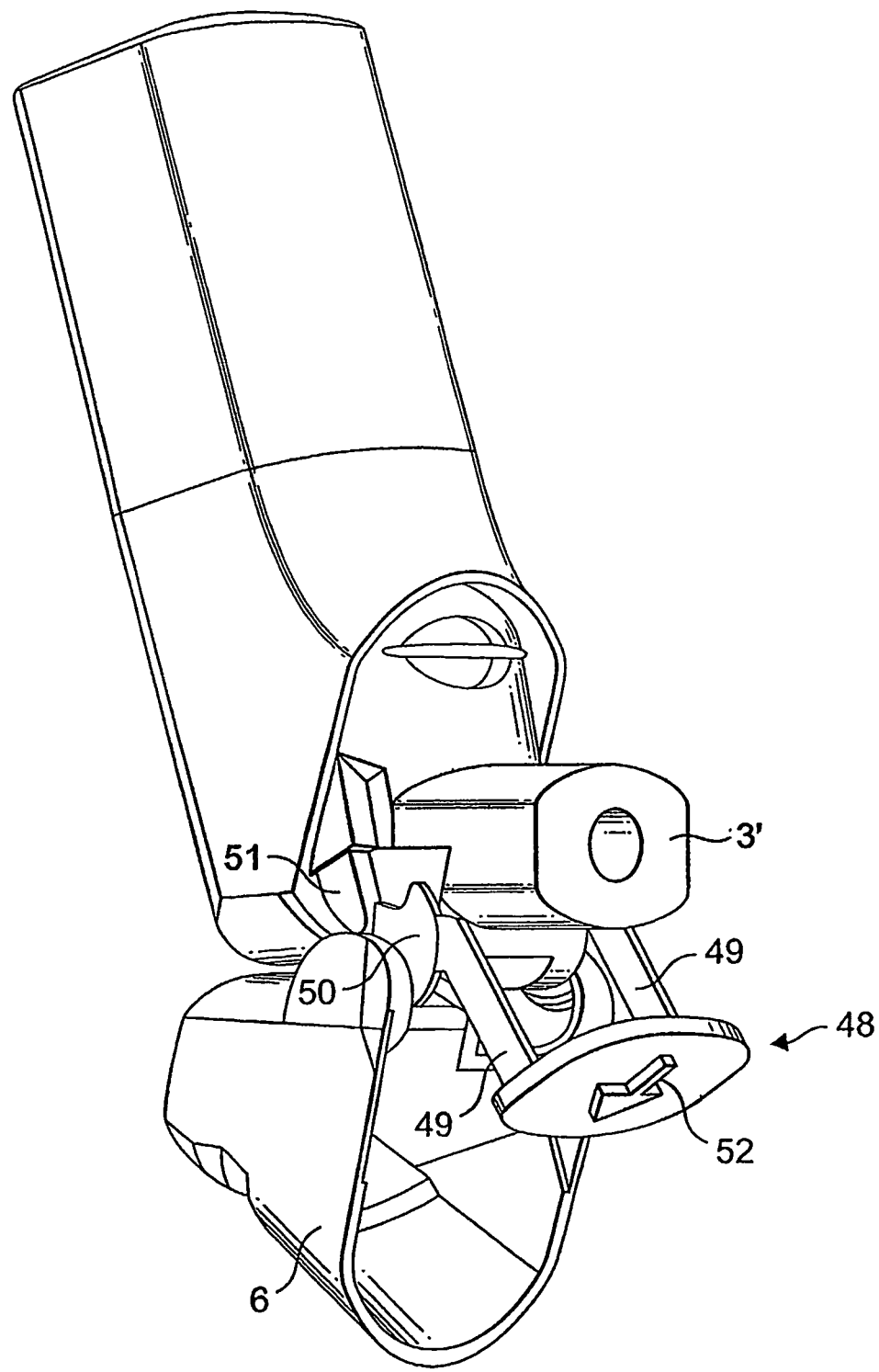
FIG. 9 shows schematically a further embodiment of inhalation device according to the invention.
Figure 10D:
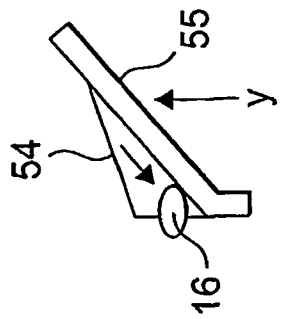
FIG. 10 shows in (a)-(d) different positions of yet further apparatus embodying the invention.
Figure 10C:
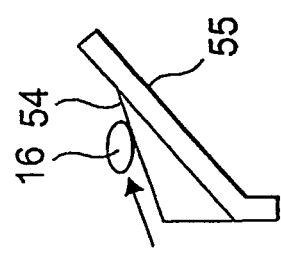
Figure 10B:
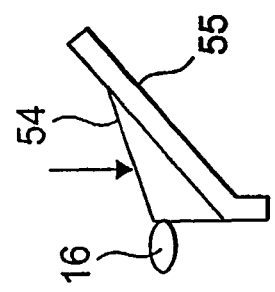
Figure 10A:
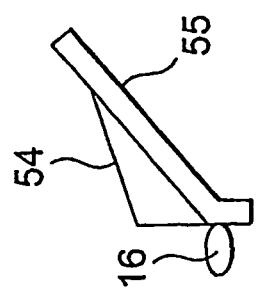

Turning now to FIG. 9, there is shown an embodiment in which the mouthpiece 3' is normally covered by a flap or disc 48 which is mounted on two arms 49 at the end of which opposite the flap or disc 48 there is a cam device 50 which operates the operating mechanism by allowing a cam follower 51 to follow the shape of the cam 50 thereby to allow the cup of the device to be charged and then for a mechanism like that labelled (5) in FIG. 3 but not shown in FIG. 9, to allow for smooth transfer of the device 4 for discharge of the inhalation dose with the medicament as described hereinbefore.

The flap, or cover 48, carries externally an indicia 52 such as an arrow to indicate to a user the direction in which the flap should be pivoted to effect operation and to expose the mouthpiece 3' for inhalation, the cover in the dosed position of the mouthpiece being itself dosed by a pivotable external cover 6.

Figure 11:
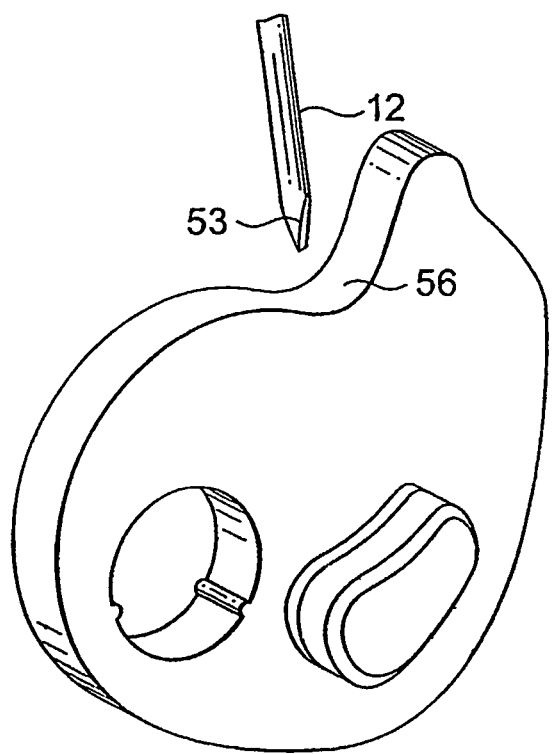
FIG. 11 shows part of actuating mechanism of the embodiment of FIG. 10.

Turning now to FIGS. 10 and 11, there is shown schematically a mechanism in which the part 16 of the device 4 is initially in the rest position shown in (a) against a ratchet part of a yoke 12 which has a lower cam 53 and which is resilient and profiled in a direction orthogonal to that as viewed, as by being convex. When that yoke 12 is actuated and pulled down for charging the cup 15 with the desired dosage of medicament, the part 16 rides up the ratchet as shown at (b) and then, to effect transfer, it moves gently and smoothly upwardly along a ramp 54 owing to the resilience and profile of the ratchet, as shown at (c). On return of the ratchet upwardly, arrow y, the part 16 of the device 4 is engaged by a downward sloping element 55 (left to right as viewed in (b)), and, in order to accommodate upward movement of the ratchet, the part 16 of the device 4 moves down the slope or return element 55 thereby returning the device 4 to the position for charging.

Figure 15:
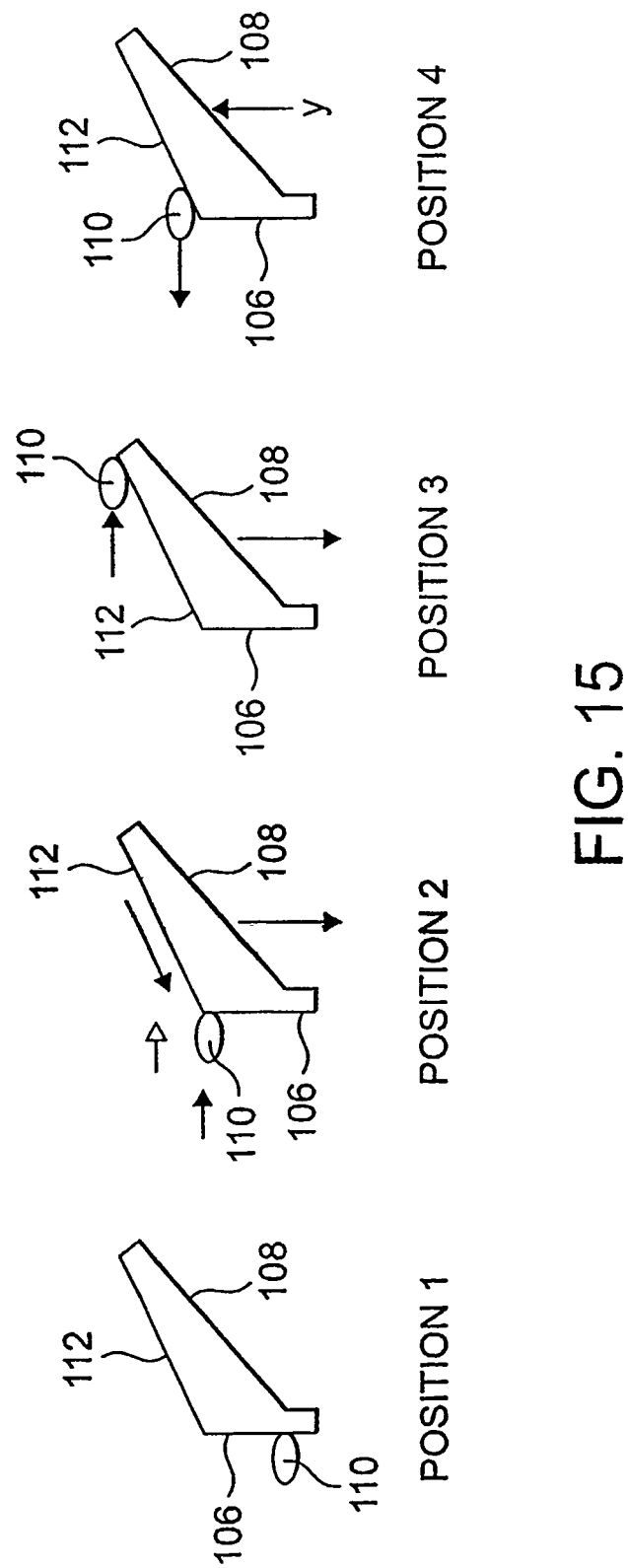
FIG. 15 shows schematically a production model apparatus similar to that shown in FIG. 10, however in this embodiment a cam of the apparatus is solid.

FIG. 15 shows schematically a production model of apparatus embodying the invention. In FIG. 15, there is shown a schematically mechanism in which the part 16 of FIG. 10 of the device 4 shown as 110 in FIG. 15, is initially in a rest position, 'position 1', against a cam part of yoke 12 which has a lower cam 53 and which is resilient and profiled in a direction orthogonal to that as viewed, as being convex. When that yoke 12 is actuated and pulled down for charging the cup 15 with the desired dosage of medicament the part 110 rides up ramp 106 of the cam, shown in 'position 2', and then, to effect transfer, it moves gently and smoothly upwardly along a ramp 112 to the inhalation position at 'position3'. On return of the yoke 12 upwardly, arrow Y, the part 110 of the device 4 returns along the ramp 112 of the cam shown in 'position 4', thereby returning the device 4 to the position for charging.

This action is exemplified in FIG. 11 where the lower end of the yoke 12, adjacent the mouthpiece, follows a single cam follower 56 of a cam which is rotatable by the mouthpiece 6, or cover 52 (FIG. 9).

Figure 12:
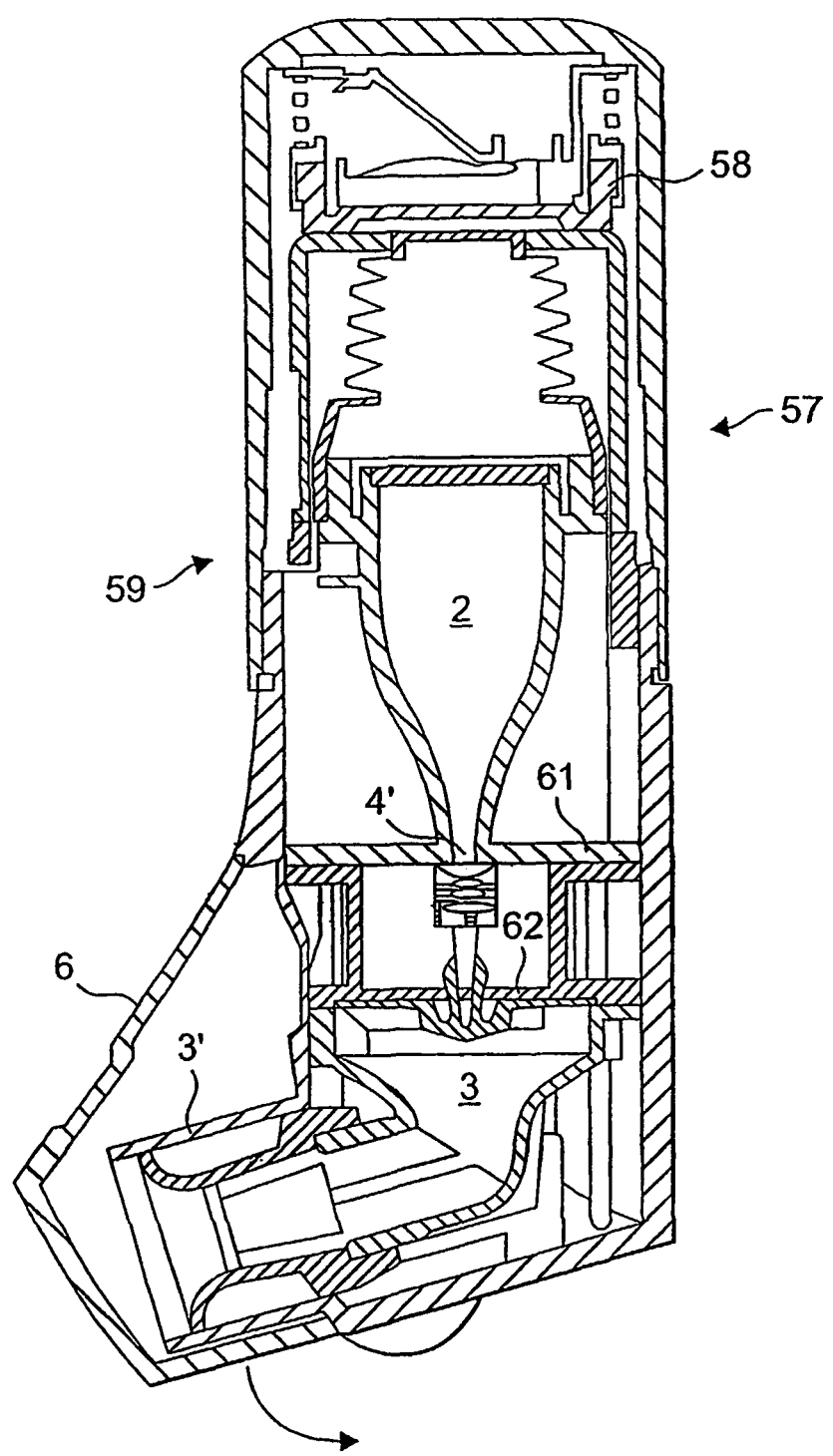
FIG. 12 shows schematically a breath operated dry powder inhalation device.
Figure 13:
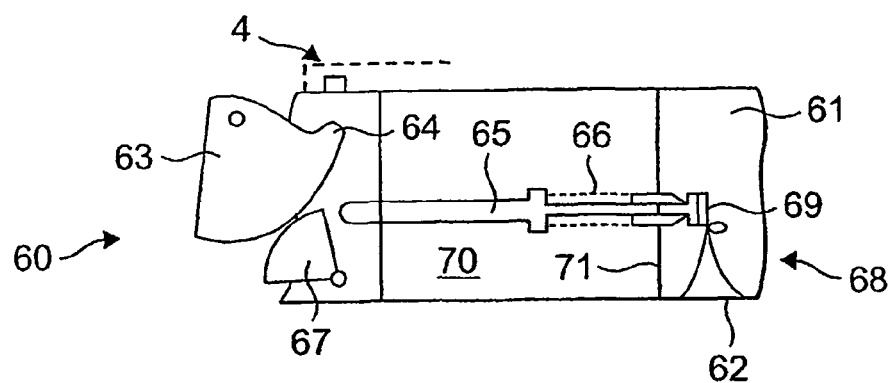
FIG. 13 shows part of the device of FIG. 12 shown in an embodiment according to the invention.

FIG. 12 shows a breath actuated dry powder inhalation apparatus 57 in which there is a force handling unit 58 on top of a lower body part 59 of the apparatus 57, the device 4 being actuable only when the patient takes a breath as known from previous breath operated examples such as that marketed under the trade mark Easi-Breathe. In this embodiment when the patient inhales a mechanism 60 shown in FIG. 13 is operative to provide for dispensation of the required dose of medicament. In this embodiment, between the upper 61 and lower 62 flanges of the reservoir 2, there is a double cam or gear arrangement, the first or upper 63 one of which as viewed has an extension 64 which engages the device 4 to hold it in the charging position, there being an elongate actuating member 65 which is operative to rotate the cam or gear 67 whereby it in turn can rotate the cam or gear 63 out of contact with the device 4 thereby allowing the device 4 to move for inhalation.

The elongate member 65 is mounted under pressure of a spring 66 there being a valve and seal arrangement 68 operable when a patient breathes on the mouthpiece to lift a flap valve 69 thereof, thereby allowing atmospheric air to enter a space 70 defined between the upper and lower flanges 61, 62 of the reservoir and between a wall 71 spacing those two flanges apart so that the spring 66, under the pressure of which the elongate member is mounted, is retracted thereby, the air pressure either side of the wall being equalised.

Figure 14:
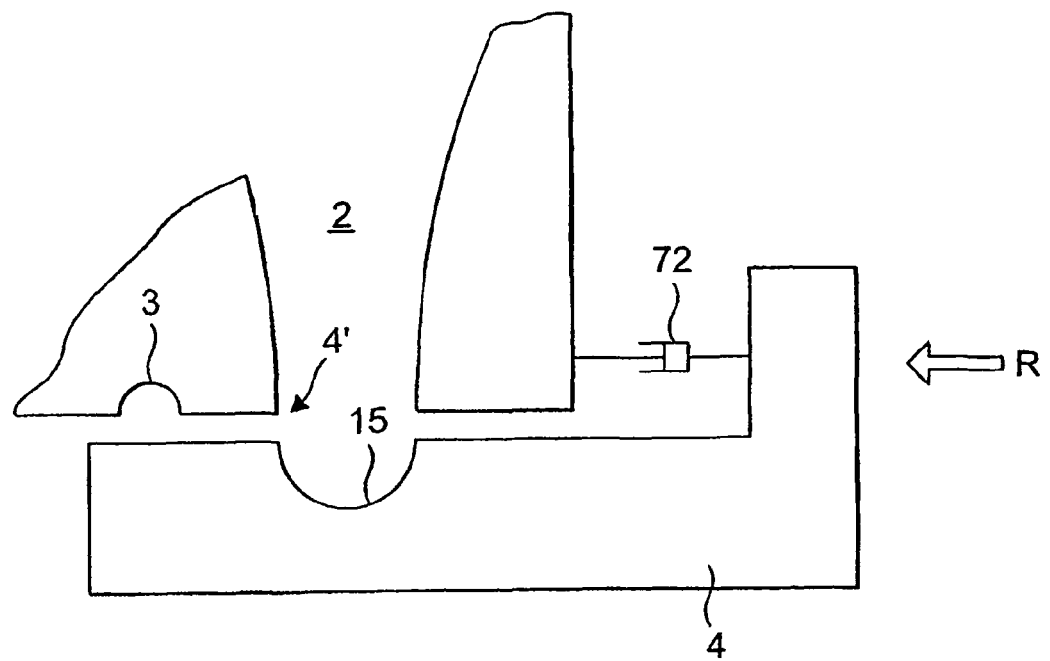
FIG. 14 shows a way of mounting the device of the apparatus of the previously described embodiment.

Turning now to FIG. 14, this shows schematically the device 4 mounted underneath the charging opening 4' from the reservoir 2 so that the cup 15 is aligned with that charging opening. The device 4 is mounted under pressure of a spring to return to the position shown, there is also a damper device 72 such as a dash pot which on operation of the mechanism to move the device longitudinally bodily to the left as shown by the arrow 'R', is active to provide a smooth, controlled passage from the charging opening to the air channel, for inhalation of the desired predetermined dose of powdered medicament.

All the embodiments herein described with reference to the accompanying drawings describe dry powder inhalation apparatus which provides for charging of a cup of a discharge device without compaction and for smooth and controlled transfer of the device to air channels thereby avoiding compaction and or spillage, so that on repeated operation, the desired metered dose will be dispensed each time a patient uses the apparatus.

It will be understood that the controlled smooth movement of the embodiments of the invention described herein does not affect individual doses dispensed when a patient uses the apparatus on inhalation. The apparatus seeks to prevent inadvertent multiple dosing as a result of multiple actuations before use by a patient. In this preferred embodiment, (FIG. 15), the controlled smooth movement changes the method by which the prior art slide carrier is transferred to the inhalation position. Instead of suddenly releasing the slide carrier as the yoke lower descends, the trigger component for the second zone has a sloped portion instead of the ledge in the second zone of the prior mechanism. The first zone remains the same as the previous design, a sudden drop generates the metering pulse from the bellows.

As the yoke lower reached the second zone the movement is controlled by the opening of the mouthpiece cover. The yoke lower ledge has also been replaced by a slope. This controls the position of the slide carrier. The slide carrier position during transfer is now linked to the mouthpiece cover. Instead of the sudden stop against the hopper upper part, the slide carrier is gradually allowed to transfer across to the inhalation position, and the stopping is more controlled, and very smooth.

As a result of the smooth transfer, there is no jolting of the powder, and only a very small amount, if any, is spilled. A single actuation results in the same pharmaceutical performance as the prior mechanism, the difference is apparent for multiple actuations.

What is claim is:

1. A dry powder inhalation apparatus, comprising a reservoir for medicament, a mouthpiece for insertion in the mouth of a user for inhalation of a predetermined dose of medicament, a delivery channel between a discharge outlet of the reservoir and the mouthpiece for delivering said predetermined dose of medicament, a device normally held adjacent the reservoir for receiving said predetermined dose of medicament from said discharge outlet and the device being biased by a spring force toward the delivery channel for transferring the medicament to the delivery channel under the spring force, a yoke member that translates vertically along a longitudinal axis of the apparatus upon actuation of the dry powder inhalation apparatus, a mechanism adapted to release the device and permit controlled movement of the device under the spring force to the delivery channel for said delivery, and an abutment that protrudes from the device and interacts with the yoke member to guide horizontal translation of the device between the reservoir and the delivery channel under the spring force upon release of the device by the mechanism and vertical translation of the yoke member, wherein the mechanism comprises abutment means which is movable transversely to the longitudinal axis of the apparatus to release the device for movement to the delivery channel.

2. The apparatus of claim 1, further comprising a cup for receiving the said dose and a longitudinally slidable body mounting said cup.

3. The apparatus of claim 2, wherein the abutment means comprises a resilient member which is flexible out of the path of the device.

4. The apparatus of claim 3, wherein the resilient member comprise a one piece member of substantially J- or U-configuration one limb of which is movable for releasing the device.

5. The apparatus of claim 4, wherein the movable limb has a finger-operable tab projecting from a housing of the apparatus.

6. The apparatus of claim 5, wherein the tab has indicia indicating the direction of flexing of the limb for release of the device.

7. The apparatus of claim 1, further comprising the abutment means being bodily movable by an actuation means.

8. The apparatus of claim 7, comprising mounting limbs one of which has a cam follower for following a cam which is rotatable for actuation of the yoke member which carries the actuation means in the form of a ramp up which a part at least of the device can travel for controlled movement thereof towards the delivery channel.

9. The apparatus of claim 8, the actuation means comprising an element for returning the device to the discharge outlet.

10. The apparatus of claim 9, the element comprising an inclined ledge down which the part travels to said charging position.

11. The apparatus of claim 10, wherein the yoke member comprises a lower (in use) cam which is resilient and has a surface profile.

12. The apparatus of claim 11, wherein the surface profile is convex in configuration.

13. The apparatus of claim 12, wherein the lower in use end of the yoke is adjacent the mouthpiece.

14. The apparatus of claim 7, wherein the actuation means comprises a resiliently mountable slidable member which has a tab projecting through a bore of a body of the apparatus for releasing the device.

15. The apparatus of claim 14, wherein the slidable member having indicia which can be read through the bore for indicating the position of the device.

16. The apparatus of claim 15, wherein the indicia comprises a colour code indicia.

17. The apparatus of claim 7, wherein the actuation means comprises a resiliently and pivotably mounted detent means which is shiftable bodily about its pivot axis to release the device.

18. The apparatus of claim 17, wherein the detent means has a finger grippable projection which projects there from and through a slot in the body of the apparatus for bodily shifting of the detent when the projection is moved along the slot.

19. The apparatus of claim 7, wherein the actuating means comprises a resiliently mounted plunger means which has one end projecting through a bore in a body of the device and an opposite end adapted to engage the device for shifting same bodily to said delivery channel.

20. The apparatus of claim 19, wherein the plunger means has a substantially cylindrical body member connecting the one end and the opposite end, the opposite end being enlarged relative to the body member.

21. The apparatus of claim 20, wherein there is a relatively soft cushion member of the opposite end for contacting the device.

22. The apparatus of claim 7, wherein the actuation means comprises an electrical, electronic or electro-mechanical means.

23. The apparatus of claim 22, wherein the actuation means comprises a solenoid means actuated by a switch device for actuation of the device.

24. The apparatus of claim 22, further comprising a power source for the electrical, electronic or electro-mechanical means.

25. The apparatus of claim 23, wherein the switch device is operable manually by a user.

26. The apparatus of claim 23, wherein the switch device is operable by inhalation of a breath by a user.

27. The apparatus of claim 7, further comprising a breath actuable apparatus.

28. The apparatus of claim 1, further comprising a cover for an end of the discharge channel at the mouthpiece, the cover being movable between a position covering the discharge channel and a position for discharging said dose, whereby to allow actuation of the mechanism.

29. The apparatus of claim 28, wherein the cover comprises a relatively rigid disc carried by opposed arms which at an end thereof opposite the disc mount a cam which has a profile for allowing movement of a cam follower in a direction away from the device whereby to allow operation of the actuation means for bodily movement of the abutment means.

30. The apparatus of claim 29, wherein the disc in its first mentioned position is housed within a guard of the apparatus, which guard is pivotably mounted for access to the disc.

31. The apparatus of claim 1, wherein the mechanism comprises cooperating rotatable means one of which has a detent for engaging the device and the other of which is operable to maintain the detent in engagement with the device and to allow rotation of the one means to release the detent and device.

32. The apparatus of claim 31, wherein the mechanism further comprises a stop member retractable as a user takes a breath on the mouthpiece, and adapted to release the other rotatable means and the detent.

33. The apparatus of claim 32, wherein the rotatable means comprises cam or gear means.

34. The apparatus of claim 32, wherein the stop member comprises an elongate mounted member which is biased to engage the other rotatable means and a flap valve which is operable to allow air into a space between said opposed walls to equalise air pressure inside and outside the space and bias the elongate member to operate the cam or gear means.

35. The apparatus of claim 1, wherein the device is mounted under pressure resilient means.

36. The apparatus of claim 35, wherein the pressure resilient means comprises spring means.

37. The apparatus of claim 1, further comprising a damper means for damping movement of the device.

* * * * *

UNITED STATES PATENT AND TRADEMARK OFFICE
CERTIFICATE OF CORRECTION

| | | |
|---|---|---|
| PATENT NO. | : 8,651,103 B2 | Page 1 of 1 |
| APPLICATION NO. | : 10/574386 | |
| DATED | : February 18, 2014 | |
| INVENTOR(S) | : Brian Barney, David O'Leary and Rachel Striebig | |

It is certified that error appears in the above-identified patent and that said Letters Patent is hereby corrected as shown below:

In the Specification:

Column 2, line 27, "indica" should read --indicia--;

Column 2, line 35, "indida" should read --indicia--;

Column 2, line 36, "indida" should read --indicia--;

Column 5, line 11, "indida" should read --indicia--;

Column 5, line 40, "indida" should read --indicia--;

Column 6, line 19, "dosed" should read --closed--;

Column 6, line 20, "dosed" should read --closed--.

Signed and Sealed this
Tenth Day of June, 2014

Michelle K. Lee
*Deputy Director of the United States Patent and Trademark Office*